United States Patent
Lin et al.

(10) Patent No.: US 10,646,455 B2
(45) Date of Patent: May 12, 2020

(54) USES OF HYDROXYANIGORUFONE

(71) Applicant: TCI CO., LTD, Taipei (TW)

(72) Inventors: Yung-Hsiang Lin, Taipei (TW); Chin-Hsiu Yu, Taipei (TW); Yu-Hung Su, Taipei (TW); Shan-Yu Lin, Taipei (TW); Yu-Ming Chung, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days.

(21) Appl. No.: 16/185,429

(22) Filed: Nov. 9, 2018

(65) Prior Publication Data

US 2019/0151257 A1 May 23, 2019

Related U.S. Application Data

(60) Provisional application No. 62/590,129, filed on Nov. 22, 2017.

(30) Foreign Application Priority Data

Oct. 8, 2018 (TW) .............................. 107135407 A

(51) Int. Cl.
*A61K 31/122* (2006.01)

(52) U.S. Cl.
CPC .................................. *A61K 31/122* (2013.01)

(58) Field of Classification Search
CPC .................................................... A61K 31/122
See application file for complete search history.

(56) References Cited

PUBLICATIONS

Gutierrez et al. Experimental Parasitology, 2013, vol. 135, pp. 456-458.*
Zill, Peter, et al., "Analysis of tryptophan hydroxylase I and II mRNA expression in the human brain: A post-mortem study," *J. Psychiatric Research*, 41(1-2), pp. 168-173 (2007).
Mössner, Rainald, et al., "Role of Serotonin in the Immune System and in Neuroimmune Interactions," *Brain, Behavior, and Immunity*, 12, pp. 249-271 (1998).
Ursin, Reidun, "Serotonin and sleep," *Sleep Medicine Reviews*, vol. 6, No. 1, pp. 57-69 (2002).
Kahn, Andrew M., et al., "Effects of Serotonin on Intracellular pH and Contraction in Vascular Smooth Muscle," *Circulation Research*, vol. 71, No. 6, pp. 1294-1304 (Dec. 1992).
Blundell, John E., et al., "Serotonin and Appetite Regulation, Implications for the Pharmacological Treatment of Obesity," *CNS Drugs*, 9(6), pp. 473-495 (Jun. 1998).
Meneses, Alfredo, et al., "Serotonin and emotion, learning and memory," *Rev. Neurosci.*, 23(5-6), pp. 543-553 (2012).
Duerschmied, D., et al., "The role of serotonin in haemostasis," *Hämostaseologie*, 29(4), pp. 356-359 (2009).
Montioli, Riccardo, et al., "A comprehensive picture of the mutations associated with aromatic amino acid decarboxylase deficiency: from molecular mechanisms to therapy implications," *Human Molecular Genetics*, vol. 4, No. 20, pp. 5429-5440 (2014).
Borjigin, Jimo, et al., "Biurnal variation in mRNA encoding serotonin N-acetyltransferase in pineal gland," *Nature*, vol. 378, pp. 783-785 (Dec. 21-28, 1995).
Ganguly, Surajit, et al., "Role of a pineal cAMP-operated arylalkylimine N-acetyltransferase/14-3-3-binding switch in melatonin synthesis," *PNAS*, 98(14), pp. 8083-8088 (Jul. 3, 2001).
Rath, Martin F., et al., "Melatonin Synthesis: Acetylserotonin O-Methyltransferse (ASMT) Is Strongly Expressed in a Subpopularion of Pinealocytes in the Male Rat Pineal Gland," *Endocrinology*, 157(5), pp. 2028-2040 (May 2016).

\* cited by examiner

*Primary Examiner* — Samira J Jean-Louis
(74) *Attorney, Agent, or Firm* — Christensen, Fonder, Dardi & Herbert PLLC

(57) ABSTRACT

A method for at least one of increasing the synthesis of melatonin and promoting the secretion of melatonin is provided, wherein the method comprises administering to a subject in need an effective amount of a compound of formula (I):

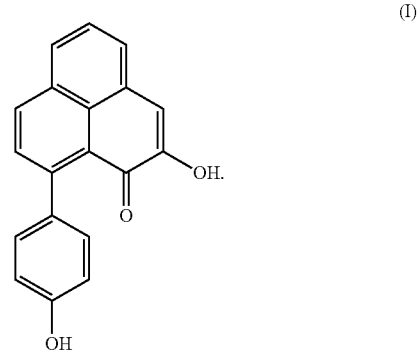

A method for at least one of treating diseases related to neurometabolic disorder, preventing diseases related to neurometabolic disorder, regulating appetite, regulating mood, regulating vasoconstriction, regulating hemostatic function and regulating immune response is also provided, wherein the method comprises administering to a subject in need an effective amount of a compound of formula (I) as described above.

2 Claims, 1 Drawing Sheet

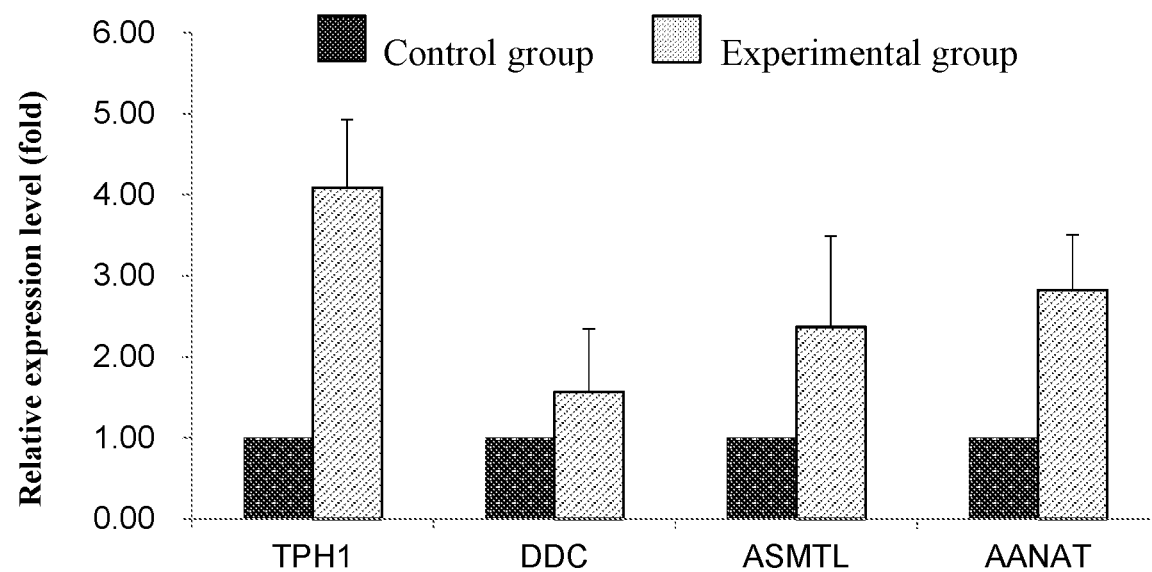

USES OF HYDROXYANIGORUFONE

CROSS REFERENCE TO RELATED APPLICATIONS

This application claims priority to U.S. Provisional Application Ser. No. 65/590,129 filed on Nov. 22, 2017, in the United States Patent and Trademark Office, and to Taiwan Patent Application No. 107135407 filed on Oct. 8, 2018, in the Taiwan Intellectual Property Office, the disclosures of which are incorporated herein in their entirety by reference.

FIELD OF THE INVENTION

The present invention relates to the use of a compound of the following formula (I) (i.e., hydroxyanigorufone), including the use of compound of formula (I) in increasing the synthesis of melatonin, and/or promoting the secretion of melatonin:

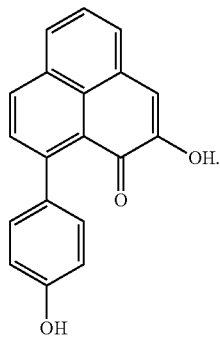

(I)

The present invention also relates to the use of compound of formula (I) in treating diseases related to neurometabolic disorder, preventing diseases related to neurometabolic disorder, regulating appetite, regulating mood, regulating vasoconstriction, regulating hemostatic function, and/or regulating immune response. The present invention also relates to the use of compound of formula (I) in increasing expression of TPH1 gene, increasing expression of DDC gene, increasing expression of AANAT gene, and/or increasing expression of ASMTL gene.

BACKGROUND OF THE INVENTION

Melatonin, which is a hormone secreted from pineal gland and serves the function of adjusting biological clock. People can stay awake during the daytime because the secretion of melatonin is suppressed by the exposure to light. On the other hand, the secretion of melatonin will increase during the nighttime and thus people can fall asleep. The secretion of melatonin in the nighttime would be insufficient if one maintains a lifestyle of working at night or irregular shifts, being nervous, and/or using electronics for a long period of time. The insufficient secretion of melatonin will reduce the sleep quality or even cause sleep disturbances (e.g., insomnia) and/or problems (e.g., feeling tired in the daytime, messing up the biological clock, decreasing the immunity), and thus seriously affect the daily life.

Medicines generally used in clinic for treating sleep disturbance include sedative-hypnotic drugs (e.g., benzodiazepine and barbiturate) and antidepressants (e.g., clomipramine and imipramine). However, the afore-mentioned medicines are prone to cause addiction and may have side effects such as hypersomnia, nausea, headache, vomiting, gastrointestinal discomfort, memory impairment, rebound insomnia, unconsciousness, ataxia, dyspnea, and/or somnambulism. Currently, melatonin being extracted from the pineal glands of cows and/or being chemically synthesized is also commercially available, while such melatonin is strictly controlled or forbidden in the countries that have concerns about mad cow disease and/or the uncertain safe dose of melatonin. Therefore, there is necessity and urgency for continuously developing a medicine or method for treating insomnia and/or ameliorating sleep disturbances effectively without causing addictions and side effects.

It was revealed that the expression of melatonin is regulated by genes such as TPH1 gene, DDC gene, AANAT gene and ASMTL gene, wherein an increased expression of TPH1 gene, DDC gene, AANAT gene, and/or ASMTL gene is helpful for increasing the synthesis of melatonin, and promoting the secretion of melatonin, thereby achieves the effects of treating insomnia, ameliorating sleep disturbance, and regulating sleep.

Inventors of the present invention discovered that a compound of the following formula (I) (i.e., hydroxyanigorufone) is effective in increasing the expression of genes such as TPH1 gene, DDC gene, AANAT gene and ASMTL gene, and thus, can be used for increasing the synthesis of melatonin and/or promoting the secretion of melatonin, thereby achieves the effects of treating insomnia, ameliorating sleep disturbances, and regulating sleep. Compound of formula (I) is also effective in treating, preventing or regulating diseases or physiological functions related to the above genes:

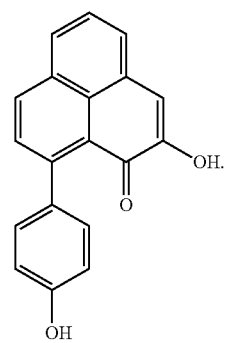

(I)

SUMMARY OF THE INVENTION

An objective of the present invention is to provide a use of a compound of the following formula (I) (i.e., hydroxyanigorufone) in the manufacture of a pharmaceutical composition, wherein the pharmaceutical composition is for increasing the synthesis of melatonin and/or promoting the secretion of melatonin:

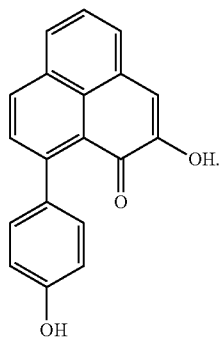

(I)

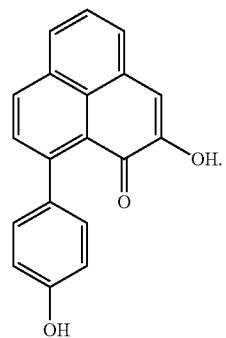

(I)

Preferably, the pharmaceutical composition is provided in a form for oral administration, transdermal administration, intravenous injection, or subcutaneous injection. Preferably, the pharmaceutical composition is for treating insomnia.

Another objective of the present invention is to provide a use of the aforesaid compound of formula (I) in the manufacture of a pharmaceutical composition, wherein the pharmaceutical composition is for at least one of treating diseases related to neurometabolic disorder, and preventing diseases related to neurometabolic disorder. Preferably, the pharmaceutical composition is provided in a form for oral administration, transdermal administration, intravenous injection, or subcutaneous injection.

Still another objective of the present invention is to provide a use of the aforesaid compound of formula (I) in at least one of ameliorating sleep disturbance, regulating appetite, regulating sleep, regulating mood, regulating vasoconstriction, regulating hemostatic function, and regulating immune response. Preferably, the compound of formula (I) is used for ameliorating sleep disturbance and/or regulating sleep, and is taken through oral, transdermal, or injection route. More preferably, the compound of formula (I) can be used in a form of food composition, wherein the food composition is a health food, a dietary supplement, a functional food, a nutritional supplement food, or a special nutritional food.

Yet another objective of the present invention is to provide a use of the aforesaid compound of formula (I) in the manufacture of a pharmaceutical composition, wherein the pharmaceutical composition is used for at least one of increasing expression of TPH1 gene, increasing expression of DDC gene, increasing expression of AANAT gene, and increasing expression of ASMTL gene. Preferably, the pharmaceutical composition is provided in a form for oral administration, transdermal administration, intravenous injection, or subcutaneous injection.

Yet another objective of the present invention is to provide a method for at least one of increasing the synthesis of melatonin and promoting the secretion of melatonin, comprising administering to a subject in need an effective amount of a compound of the following formula (I):

Preferably, the method of the present invention is for treating insomnia, ameliorating sleep disturbance, and regulating sleep. In the method according to the present invention, the compound of formula (I) can be administered as the pharmaceutical composition described above.

Yet another objective of the present invention is to provide a method for at least one of treating diseases related to neurometabolic disorder, preventing diseases related to neurometabolic disorder, regulating appetite, regulating mood, regulating vasoconstriction, regulating hemostatic function and regulating immune response, comprising administering to a subject in need an effective amount of the aforesaid compound of formula (I). In the method according to the present invention, the compound of formula (I) can be administered as the pharmaceutical composition or the food composition described above Yet another objective of the present invention is to provide a method for at least one of increasing expression of TPH1 gene, increasing expression of DDC gene, increasing expression of AANAT gene and increasing expression of ASMTL gene, comprising administering to a subject in need an effective amount of the aforesaid compound of formula (I). In the method according to the present invention, the compound of formula (I) can be administered as the pharmaceutical composition described above.

The detailed technology and preferred embodiments implemented for the present invention are described in the following paragraphs accompanying the appended drawings for people skilled in this field to well appreciate the features of the claimed invention.

BRIEF DESCRIPTION OF THE DRAWINGS

FIG. 1 shows the effect of compound of formula (I) of the present invention on increasing the expressions of TPH1 gene, DDC gene, AANAT gene and ASMTL gene, wherein cells in the "control group" were cultured in a medium free of the aforesaid compound of formula (I) for 48 hours, and those in the "experimental group" were cultured in a medium containing the aforesaid compound of formula (I) for 48 hours.

DESCRIPTION OF THE PREFERRED EMBODIMENTS

The following will describe some of the embodiments of the present invention in detail. However, without departing from the spirit of the present invention, the present invention may be embodied in various embodiments and should not be limited to the embodiments described in the specification or defined in the appended claims.

Unless otherwise indicated herein, the expressions "a," "an," "the," or the like recited in the specification of the present invention (especially in the claims) are intended to include both the singular and plural forms. The term "prevent" or "preventing" recited in this specification refers to inhibiting or preventing a particular condition of illness from breaking out, or maintaining good health in a sensitive subject to tolerate diseases. The term "treat" or "treating" recited in this specification should not be construed as treating a subject until the subject is completely recovered, but should include maintaining the progression or symptoms of the diseases in a substantially static state, increasing the recovery rate of a subject, alleviating the severity of a particular condition of illness, or increasing the life quality of patients. The term "regulate" or "regulating" recited in this specification refers to upregulating (includes inducing, stimulating, and enhancing) or downregulating (includes inhibiting and weakening) the physiological functions in a subject toward a normal state. The term "subject" recited in this specification refers to a mammalian, including human and non-human animals.

It is known that TPH1 gene is mainly involved in the synthesis of serotonin, which is related to physiological functions such as appetite, sleep, mood, vasoconstriction, hemostatic function and immune response. Accordingly, the decreased expression of TPH1 gene will affect the above physiological functions related to serotonin, and these can be noted in such as "Analysis of tryptophan hydroxylase I and II mRNA expression in the human brain: a post-mortem study. *J Psychiatr Res.* 2007 January-February; 41(1-2):168-73," "Role of Serotonin in the Immune System and in Neuroimmune Interactions. BRAIN, BEHAVIOR, AND IMMUNITY 12, 249-271 (1998)," "Serotonin and sleep. Sleep Medicine Reviews, Vol. 6, No. 1, pp 57-69, 2002," "Effects of Serotonin on Intracellular pH and Contraction in Vascular Smooth Muscle. Circulation Research Vol 71, 1992, 1294-1304," "Serotonin and Appetite Regulation. CNS Drugs 1998 June; 9 (6): 473-495," "Serotonin and emotion, learning and memory. Rev. Neurosci. 2012; 23(5-6): 543-553," and "The role of serotonin in haemostasis. Hamostaseologie. 2009 November; 29(4):356-9," which are entirely incorporated hereinto by reference. Therefore, if the expression of TPH1 gene can be increased, the above physiological functions related to serotonin can be regulated.

It is known that DDC gene is involved in the synthesis of melatonin, and the deficiency of DDC gene will also lead to neurometabolic disorder, and these can be noted in such as "A comprehensive picture of the mutations associated with aromatic amino acid decarboxylase deficiency: from molecular mechanisms to therapy implications. *Hum Mol Genet.* 2014 Oct. 15; 23(20):5429-40," which is entirely incorporated hereinto by reference. Therefore, if the expression of DDC gene can be increased, the diseases related to neurometabolic disorder can be treated or prevented, and the physiological functions related to the synthesis of melatonin can be regulated.

It is known that AANAT gene plays an important role in the synthesis of melatonin, and these can be noted in such as "Diurnal variation in mRNA encoding serotonin N-acetyltransferase in pineal gland. *Nature.* 1995 Dec. 21-28; 378 (6559):783-5," and "Role of a pineal cAMP-operated arylalkylamine N-acetyltransferasey14-3-3-binding switch in melatonin synthesis. PNAS Jul. 3, 2001. 98 (14) 8083-8088," which are entirely incorporated hereinto by reference. Therefore, if the expression of AANAT gene can be increased, the physiological functions related to the synthesis of melatonin can be regulated.

It is known that ASMTL gene is the key gene being responsible for the latest catalytic step of the synthesis pathway of melatonin, and these can be noted in such as "Melatonin synthesis: Acetylserotonin Omethyltransferase (ASMT) is strongly expressed in a subpopulation of pinealocytes in the male rat pineal gland. *Endocrinology.* 2016 May; 157(5):2028-40," which is entirely incorporated hereinto by reference. Therefore, if the expression of ASMTL gene can be increased, the physiological functions related to the synthesis of melatonin can be regulated.

Inventors of the present invention incidentally discovered that the compound of the following formula (I) could effectively increase the expressions of TPH1 gene, DDC gene, AANAT gene and ASMTL gene:

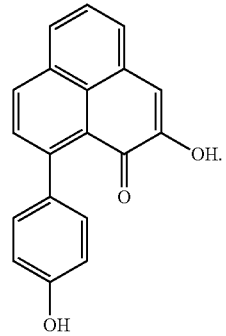

(I)

Therefore, the present invention relates to the use of compound of formula (I), including: using the compound of formula (I) in ameliorating sleep disturbance, regulating appetite, regulating sleep, regulating mood, regulating vasoconstriction, regulating hemostatic function and/or regulating immune response, using the compound of formula (I) in manufacturing a pharmaceutical composition, and providing a method of administering to a subject in need an effective amount of the compound of formula (I). The pharmaceutical composition and method provided in accordance with the present invention are also for increasing expression of TPH1 gene, DDC gene, AANAT gene and/or ASMTL gene.

The compound of formula (I) adopt in accordance with the present invention could be obtained from any suitable source. For example, the compound of formula (I) could be purchased from the market, be purified and isolated from the extract of plant(s), or be obtained by a chemical synthesis. For example, the compound of formula (I) could be purchased from the ChemFaces company (Rainbow Biotechnology CO., LTD).

The pharmaceutical composition provided in accordance with the present invention could be administered to a subject in need systemically or topically, and could be delivered by various drug delivery systems (DDSs), such as oral drug delivery system, transdermal drug delivery system, injectable drug delivery system, etc. For example, to enhance bioavailability, control drug release speed, target the lesion precisely and reduce side effects, the pharmaceutical composition could be delivered by a liposome, a microcapsule, nanoparticles, microneedles, but is not limited thereby.

Depending on the desired purpose(s), the pharmaceutical composition of the present invention could be provided in any suitable form without particular limitations. For example, the pharmaceutical composition could be provided in a form suitable for administering to a subject in need by an oral or parenteral (such as transdermal, intravenous injection, and subcutaneous injection) route, but is not limited thereby. Depending on the form and purpose(s), a suitable carrier could be chosen and used to provide the pharmaceutical composition. Examples of the carrier include excipients, diluents, auxiliaries, stabilizers, absorbent retarders, disintegrating agents, hydrotropic agents, emulsifiers, antioxidants, adhesives, binders, tackifiers, dispersants, suspending agents, lubricants, hygroscopic agents, etc.

As a form for oral administration, the pharmaceutical composition of the present invention can comprise any pharmaceutically acceptable carrier that will not adversely affect the desired effects of the active ingredient (i.e., the compound of formula (I)). Examples of the suitable carrier include, but are not limited to, water, saline, dextrose, glycerol, ethanol or its analogs, cellulose, starch, sugar bentonite, and combinations thereof. The pharmaceutical composition could be provided by any suitable method in any suitable form for oral administration, such as in the form of a tablet (e.g., dragee), a pill, a capsule, a granule, a pulvis, a fluidextract, a solution, syrup, a suspension, or a tincture, but is not limited thereby.

As a form for transdermal administration, the pharmaceutical composition of the present invention could be provided in a form of a patch, an emulsion, a cream, a gel (such as a hydrogel), a paste (such as a dispersing paste, an ointment), a spray, or a solution (such as a suspension) for external use, but is not limited thereby.

As for the form of injection or drip suitable for subcutaneous or intravenous injection administration, the pharmaceutical composition may comprise one or more ingredient(s), such as an isotonic solution, a salt-buffered saline (e.g., phosphate-buffered saline or citrate-buffered saline), a hydrotropic agent, an emulsifier, 5% sugar solution, and other carriers to provide the pharmaceutical composition as an intravenous infusion, an emulsified intravenous infusion, a powder for injection, a suspension for injection, or a powder suspension for injection. Alternatively, the pharmaceutical composition may be prepared as a pre-injection solid. The pre-injection solid can be provided in a form which is soluble in other solutions or suspensions, or in an emulsifiable form. A desired injection is provided by dissolving the pre-injection solid in other solutions or suspensions or emulsifying it prior to being administered to a subject in need.

Depending on the needs, age, body weight and health conditions of the subject, the pharmaceutical composition provided in accordance with the present invention could be administered at various administration frequencies, such as once a day, multiple times a day, or once every few days, etc. In addition, the amount of compound of formula (I) in the pharmaceutical composition could be adjusted depending on the requirements of practical application. Optionally, the pharmaceutical composition provided in accordance with the present invention could further comprise one or more other active ingredients (e.g., hypnotic drugs, antidepressants, and melatonin), or to be used in combination with a medicament comprising one or more other active ingredients, to further enhance the effects of the pharmaceutical composition, or to increase the application flexibility and adaptability of the preparation thus provided, as long as the other active ingredients will not adversely affect the desired effects of the active ingredients of the present invention (i.e., the compound of formula (I)).

Optionally, the pharmaceutical composition and the food composition provided in accordance with the present invention could further comprise a suitable amount of additives, such as a flavoring agent, a toner, or a coloring agent for enhancing the palatability and the visual perception of the pharmaceutical composition or the food composition, and/or a buffer, a conservative, a preservative, an antibacterial agent, or an antifungal agent for improving the stability and storability of the pharmaceutical composition or the food composition.

The food composition provided in accordance with the present invention can be a health food, a dietary supplement, a functional food, a nutritional supplement food or a special nutritional food, and can be manufactured as dairy products, meat products, breadstuff, pasta, cookies, troche, capsule, fruit juices, teas, sport beverages, nutritional beverages, etc., but is not limited thereby. Preferably the food composition provided in accordance with the present invention is a health food.

Depending on the age, body weight and healthy conditions of the subject, the health food, dietary supplement, functional food, nutritional supplement food and special nutritional food provided in accordance with the present invention could be taken at various frequencies, such as once a day, several times a day or once every few days, etc. The amount of the compound of formula (I) in the health food, dietary supplement, functional food, nutritional supplement food and special nutritional food provided in accordance with the present invention could be adjusted, preferably to the amount that it should be taken daily, depending on the specific population.

The recommended daily dosage, use standards and use conditions for a specific population (e.g., patient with insomnia, patient with depression, and pregnant woman), or the recommendations for a use in combination with another food product or medicament can be indicated on the exterior package of the health food, dietary supplement, functional food, nutritional supplement food and/or special nutritional food provided in accordance with the present invention. Thus, it is suitable for the user to take the health food, dietary supplement, functional food, nutritional supplement food and/or special nutritional food by him- or herself safely and securely without the instructions of a doctor, pharmacist, or related executive.

The present invention also provides a method for increasing the synthesis of melatonin and/or promoting the secretion of melatonin, comprising administering to a subject in need an effective amount of the aforesaid compound of formula (I), wherein the term "a subject in need" refers to a subject having an insufficient synthesis and/or secretion of melatonin. The present invention also provides a method for treating diseases related to neurometabolic disorder, preventing diseases related to neurometabolic disorder, regulating appetite, regulating mood, regulating vasoconstriction, regulating hemostatic function and/or regulating immune response, comprising administering to a subject in need an effective amount of the aforesaid compound of formula (I), wherein the term "a subject in need" refers to a subject suffering from neurometabolic disorder-related diseases, an increased appetite, a poor appetite, a mood disorder, vasoconstrictor abnormalities, hemostatic abnormalities and/or an abnormal immune response. In the above method, the compound of formula (I) could be administered to the subject in need as a pharmaceutical composition or a food composition as described above, and the administration type, administration route, administration form, administration frequency and uses of the pharmaceutical composition and the food composition are also all in line with the above descriptions.

The present invention also provides a method for increasing expression of TPH1 gene, increasing expression of DDC gene, increasing expression of AANAT gene and/or increasing expression of ASMTL gene, comprising administering to a subject in need an effective amount of the aforesaid compound of formula (I), wherein the term "a subject in need" refers to a subject whose TPH1 gene, DDC gene, AANAT gene and/or ASMTL gene is deleted, mutated, or low-expressed. In this method, the compound of formula (I) could be administered to the subject in need as a pharmaceutical composition described above and the administration type, administration route, administration form, administration frequency and uses of the pharmaceutical composition are also all in line with the above descriptions.

The present invention will be further illustrated in detail with specific examples as follows. However, the following examples are provided only for illustrating the present invention and the scope of the present invention is not limited thereby. The scope of the present invention will be indicated in the appended claims.

EXAMPLES

The sources of materials used in the following Examples are as follows:
1. Compound of formula (I) of the present invention: purchased from ChemFaces company (Rainbow Biotechnology CO., LTD), product number: CFN96877, CAS number: 56252-02-9.
2. SHSYSY cell: purchased from ATCC, product number: CRL-2266.
3. DMEM medium: containing 90% DMEM, 10% FBS and 1% Penicillin/Streptomycin, wherein DMEM was purchased from Gibco (product number: 12100-046), FBS was purchased from Gibco (product number: 10437-028) and Penicillin/Streptomycin was purchased from Gibco.
4. RNA Extraction Kit: purchased from Geneaid.
5. Reverse transcriptase (SuperScript® III Reverse Transcriptase): purchased from Invitrogen company.
6. KAPA SYBR FAST qPCR kit: purchased from KAPA Biosystems company.
7. Step One Plus system: purchased from ABI company.

Example 1

SHSY5Y cells were seeded in a 6-well plate ($1\times10^5$ cells/well) and then cultured for 24 hours. Thereafter, cells were divided into the control group and experimental group and were separately cultured in the following medium for 48 hours:
1. Control group: DMEM medium;
2. Experimental group: a medium the same as that of the control group, but additionally added with 0.0625 µg/ml of the compound of formula (I).

Thereafter, cells of the above groups were harvested and subjected to an RNA extraction with an RNA Extract Kit. The RNA thus obtained was then transcribed into cDNA by using a Reverse Transcriptase. Thereafter, the cDNA was subjected to a quantitative polymerase chain reaction (qPCR) by using a Step One Plus system and a KAPA SYBR FAST qPCR kit to determine the expression levels of genes related to melatonin (including TPH1, DDC, AANAT and ASMTL) in the cells of each group.

The above experimental steps were repeated three times, and then the results of the three experiments were averaged. Thereafter, the result of the control group was used as a basis (i.e., the gene expression level of the control group was set as 1-fold) to calculate the relative gene expression level of the experimental group. The results are shown in FIG. 1.

As shown in FIG. 1, as compared to the control group, the expression levels of TPH1, DDC, AANAT and ASMTL genes in the cells of the experimental group all significantly increased. These results indicate that the compound of formula (I) of the present invention is effective in increasing the synthesis of melatonin and promoting the secretion of melatonin. Hence, the compound of formula (I) of the present invention can be used for treating insomnia, ameliorating sleep disturbances, treating diseases related to neurometabolic disorder, preventing diseases related to neurometabolic disorder, regulating appetite, regulating sleep, regulating mood, regulating vasoconstriction, regulating hemostatic function and regulating immune response, especially for treating insomnia, ameliorating sleep disturbances, and regulating sleep.

What is claimed is:

1. A method for at least one of increasing expression of TPH1 gene, increasing expression of DDC gene, increasing expression of AANAT gene and increasing expression of ASMTL gene, comprising administering to a subject in need an effective amount of a compound of formula (I):

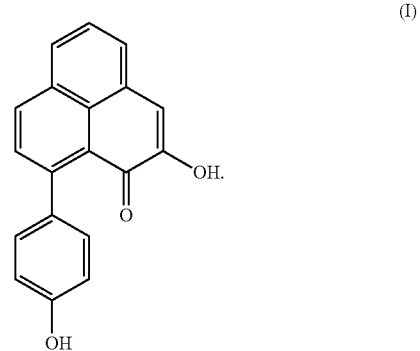 [SMILES: O=C1C(O)=Cc2cccc3ccc(-c4ccc(O)cc4)c1c23]

2. The method as claimed in claim 1, wherein the compound of formula (I) is administered to the subject by at least one of oral administration, transdermal administration, intravenous injection, and subcutaneous injection.

* * * * *